United States Patent [19]

Kobayashi et al.

[11] Patent Number: 5,139,947

[45] Date of Patent: Aug. 18, 1992

[54] ANTIGENIC NONINFECTIOUS HIV-PRODUCING CLONED T CELL

[75] Inventors: Nobuyuki Kobayashi; Yoshiaki Hamamoto; Naoki Yamamoto, all of Ube, Japan

[73] Assignee: Banyu Pharmaceutical Co., Ltd., Tokyo, Japan

[21] Appl. No.: 414,368

[22] Filed: Sep. 29, 1989

[30] Foreign Application Priority Data

Feb. 2, 1989 [JP] Japan .................................. 1-24703

[51] Int. Cl.$^5$ .............................................. C12N 5/10
[52] U.S. Cl. ................................ 435/240.26; 436/543; 436/811; 435/7.2; 435/7.24; 435/974; 435/69.3; 435/70.1; 435/5
[58] Field of Search ............ 435/7.2, 7.24, 69.1, 435/69.3, 70.1, 240.26, 974, 69.3, 5; 436/543, 811; 530/387, 829

[56] References Cited

PUBLICATIONS

Popovic, et al., Detection, Isolation & Continuous . . . Pre-AIDS Science 224, 497–500, May 1984.
Harada et al., Infection of HTLV-III/LAV in HTLV-I . . . Assay Science 229, 563–566, Aug. 1985.
Tsai et al., Inhibition of HIV Infectivity by Chloroquine, Int. Conf. on AIDS, Jun. 4–9, 1989 Abstract Only.

Primary Examiner—Christine Nucker
Assistant Examiner—Jeffrey Stucker
Attorney, Agent, or Firm—Wegner, Cantor, Mueller & Player

[57] ABSTRACT

The invention is a cloned T cell prepared by infecting a human T cell, H9, with HTLV-III B, which cloned human T cell is antigenic for HTLV-III B, does not have a syncytium-forming activity, and does not produce infectious HTLV-III B virions.

4 Claims, 7 Drawing Sheets

ANTIGENIC NONINFECTIOUS HIV-PRODUCING CLONED T CELL

BACKGROUND OF THE INVENTION

1. Field of the Invention

The present invention relates to antigenic noninfectious acquired immunological deficiency syndrome (AIDS) viruses (also referred to as human immunodeficiency virus, HIV), cloned human T cells producing the antigenic noninfectious HIV, and use of the antigenic noninfectious HIV and the cloned cells. Since the present HIV viruses are noninfectious but still antigenic, they can be used as safe and effective HIV antigen in the field of diagnosis, and therapy of AIDS. Moreover, since the present cloned T cells produce the antigenic HIV but do not form syncytia, the cells as such are promising for use as a safe live vaccine for the HIV.

2. Description of the Related Art

For the treatment of AIDS caused by the infection of human immunodeficiency virus (HIV), currently interleukins, interferons, azidothymidine (AZT) and the like are used, but these have not been fully evaluated, and in practice are not truly effective agents.

Accordingly, a vaccine therapy is now urgently sought as an effective prophylactic and therapeutic treatment method for AIDS. For vaccine therapy, it is essential to obtain an extremely safe antigen essential for the production of an antibody to HIV. At present, as a method of producing such an antigen, the use of transformed cells which are antigenic but noninfectious is under investigation. For example, Ikuta et al., Jpn. J. Cancer Res. (Gann), 79, 418–423, April 1988, reported a transformed cell line derived from a human T cell MT-4 line. But, the MT-4 cell line was originally derived from a cell infected with HTLV-1, which is an etiologic virus for adult T cell leukemia, and therefore, is per se pathogenic. Moreover, although the transformed cell derived from MT-4 produces noninfectious virions, since it has a syncytium forming ability, it is not practical as vaccine material. Note, the syncytium forming ability, in the present case, is an ability of a transformed cell to fuse with nomal T cells to form a multi-nuclear cell, resulting in the death of the cell.

Another approach to obtain an antibody to HIV is to genetically produce a protein fragment derived from HIV. This approach is not particularly desirable, as it is considered that the antigenic potency of the immunogenic protein fragment is weaker than that of whole HIV. Moreover, since whole HIV contains various antigens, it provides various antibodies to HIV and provides an extremely potent vaccine. An antigenic protein fragment does not have this advantage.

Regarding the diagnosis of AIDS, since it is reported that many cases of AIDS are caused by a transfusion of blood infected with HIV, sera from blood donors are screened by an enzyme-linked immunoadsorbent assay (ELISA), immuno blotting or agglutination test prior to use of the blood. These assay methods, however, require a purified virion or protein isolated from cells infected with HIV, as antigen to detect the antiserum to HIV. To prepare such a virus antigen, however, a large amount of infectious HIV or tissue culture product containing HIV (several hundred litters per week) must be processed, requiring operators to be continuously exposed to materials infected with HIV, and thus to be continually under a potential risk of infection by HIV.

Further, in this diagnosis of AIDS, even if the results of the above-mentioned assays are positive, this does not always mean that the subject has AIDS, and therefore, it is considered that a confirmatory diagnosis must be made. To make this confirmatory diagnosis, an indirect immunofluorescence technique is known whereby HIV-infected cells reacted with a serum sample taken from a patient, further reacted with a fluorescence-labeled second antibody, and the HIV-infected cells thus treated then microscopically observed. In this assay, where the serum sample of patient contains an antibody to the virus, the HIV-infected cell generates a fluorescence. Nevertheless, since this assay uses HIV-infected cells, the operator is still at risk of infection by HIV, and therefore, this technique is not widely used on a routine test.

SUMMARY OF THE INVENTION

Accordingly, the object of the present invention is to provide HIV derivatives which simultaneously satisfy the requirements that they are HIV antigenic and noninfectious; human T cell lines which produce this HIV derivative, but do not form syncytia; and the use of the HIV derivatives and the human T cell lines.

More specifically, the present invention provides a cloned human T cell in which a noninfectious HIV gene has been incorporated, which cell does not have a syncytium-forming ability.

The present invention also provides a process for producing a cloned human T cell, comprising the steps of preparing human T cells;
infecting the human T cells with HIV; and
cloning and selecting a cell which is HIV-antigenic and does not have a syncytium-forming ability.

The present invention moreover provides a mutant HIV which is HIV antigenic and noninfectious.

The present invention still further provides a process for the production of a mutant HIV which is HIV-antigenic and noninfectious, comprising culturing the above-mentioned cloned human T cells, and recovering the mutant HIV from the culture.

The present invention also provides a prophylactic or therapeutic agent for AIDS, comprising the above-mentioned cloned human T cells or mutant HIV.

Moreover, the present invention provides an assay kit for detecting an anti-HIV antibody comprising the above-mentioned cloned human T cells or mutant HIV.

The present invention also provides an assay method for detecting an anti-HIV antibody, comprising specifically reacting the anti-HIV antibody in a sample with the above-mentioned cloned human T cells or mutant HIV.

The present invention still further provides a safe method of screening prophylactic and therapeutic agents for AIDS, characterized by using the above-mentioned cloned T cells or mutant HIV.

BRIEF EXPLANATION OF THE DRAWINGS

FIGS. 4-1 to 4-3 show the results of Southern blot hybridization of Sac I fragments (4-1), Bgl II fragments (4-2) and EcoR I fragments (4-3) of DNAs derived from an H6 cell (lane a), M10 cell (lane b) and M12 cell (lane c), using, in all cases, Sac I fragment of plasmid pNK5.2 as a hybridization probe. The numbers on the right show the molecular weights (K bp) of the molecular weight marker (λDNA Hind III fragments);

FIGS. 5-1 and 5-2 are electronographs of virions formed by an H6 cell (5-1) and M10 cell (5-2); and, FIG. 6 shows the results of an indirect immunofluorescence assay of serum from an AIDS patient using H6 cells.

DESCRIPTION OF THE PREFERRED EMBODIMENT

According to the present invention, there are provided mutant HIVs which are noninfectious but still antigenic. These mutant HIVs are produced by cloned human T cells infected with HIV. The cloned human T cells are prepared by infecting human T cells with HIV and cloning cells which produce the desired mutant HIV.

As starting materials, human T cells, preferably established human T cellline, are used. As examples of the starting T cells, the T cell line H9 is mentioned.

As a second starting material, used to obtain HIV-infected human T cells producing the mutant HIV, any HIV strain can be used.

The starting human T cells can be cultured and maintained according to a well known procedure established for culturing human T cells. For example, T cells can be grown in RPMI 1640 supplemented with 10% fetal calf serum, D-MEM supplemented with 10% FCS, or the like. The cells are preferably cultured at a temperature of about 37° C., and under the presence of about 5% carbon dioxide introduced in air. The infection of the starting T cells with HIV is carried out according to a conventional procedure, for example, as described by Harada, S. et al., Science 229, 563-566 (1985). This infection is carried out at an m.o.i. of 0.0001 to 1 PFU/cell, preferably 0.001 to 0.01 PFU/cell, for example at 0.001 PFU/cell.

The process of cloning and selecting the infected cells is described in detail in Example 1, in which the characterization of the selected T cells and the mutant HIV is also described, in detail.

Since the present mutant HIV is noninfectious and antigenic, it can be used an ingredient of a live vaccine for AIDS. Moreover, it is useful as a reagent in a diagnostic assay for AIDS, for example, ELISA, immuno blotting, aggregation, immunofluorescence, hybridization probe, and the like. The present HIV-infected cells do not form syncytia, and therefore, are extremely safe. Accordingly, the present HIV-infected T cells are useful as an ingredient of a live vaccine and a reagent for a diagnostic assay for AIDS. This assay includes the above-mentioned various assays, and as these assays are well known, the assays of the present invention can be easily carried out by replacing conventional HIV, which is infectious and antigenic, or cells producing the infectious HIV, with the present noninfectious but antigenic HIV or the present HIV-infected T cells which no longer have a syncytium-forming ability, respectively.

For example, in ELISA using the present mutant HIV or the HIV infected T cells, HIV particles harvested from H6 cells by sucrose density gradient centrifugation or disrupted cell lysate fractionated by anti-HIV antibody-coupled affinity column were coated on, a 96 wells microtiter plate (Nunc). The antigen-coated plate was then reacted with appropriately diluted human serum for 1 hr. at 37° C. The plate were next reacted with peroxidase conjugated anti-human IgG for 1 hr. After extensive washing of the plate, anti-human IgG trapped in the each well of the plate was reacted with o-phenylene-diamine solution for 30 min. The reaction was terminated by adding 1 N $H_2SO_4$ and quantitated by spectrophotometer at 492 nm.

In Immuno blotting, either disrupted H6 lysate or HIV particles purified from H6 cells were denatured by SDS-sample buffer (Laemmli, U.K. Nature, 227, 680-685 (1970)) and separated by 12% SDS polyacrylamide gel electronphoresis. After electrophoresis, proteins in the gel were electrophoretically transfered to nitrocellulose filter (BA85, S&S) by the method of Towbin et al (Towbin, H. et al, Proc. Natl. Acad. Sci. USA., 76, 4350 (1979)). The filter was then reacted with human sera for the detection of anti-HIV antibody.

In Immunofaluorescence, H6 cells were washed with 10 mM phosphate buffered saline, pH 7.2 twice and then spotted on a 12 wells Multitest Slide (Flow) and air dried. After fixing in 100% methanol at −20° C. for 10 min, each well of the slide was reacted with human serum for 30 min at 37° C. The wells were then reacted with FITC conjugated goat anti-human IgG (Cappel) for 30 min at 37° C. After extensive washing, the plate was examined for the presence of anti-HIV antibody by fluorescence microscope.

EXAMPLES

The present invention will now be further illustrated by, but is by no means limited to, the following examples.

EXAMPLE 1

Construction of HIV infected T cells, production of noninfectious mutant HIV, and characterization thereof As a starting HIV material, a culture supernatant of a HIV-persistently infected cell MOLT-4/HIV HTLVIIIB (Matsuyama, T et al., Jpn. J. Cancer Res., 79, 156-159 (1988)) was used. As the starting human T cell lines, a MOLT-4 line (Minowada, J. et al., J. Natl, Cancer Inst., 49. 891-895 (1972)) and H9 line (Popovic M. et al., Science, 224. 497-500, (1984)) were used. Then, according to a method of Harada et al., Science, 229, 563-566 (1985), the MOLT-4 and H9 cells were infected with the culture supernatant of MOLT-4/$HIV_{HTLVIIIB}$ at an m.o.i. of 0.001 PFU/cell. The thus-infected cells were cultured in RPMI 1640 supplemented with 10% fetal calf serum in an atmosphere of air containing 5% $CO_2$, at 37° C. for 4 to 5 weeks, to obtain a suspension of HIV persistently-infected cells. The cell suspension was distributed to each well of a 96-well plate in an amount of 0.6 cell/well, and cells in each well were passaged while monitoring an extent of the cell growth. Tests of the cloned cells from each well were made to determine whether they are HIV-infected cells, on the basis of expression of an HIV antigen, by the indirect immunofluorescence technique. Namely, cloned cells from each well were smeared on a slide glass for microscopy, air-dried, and fixed with cold methanol. The fixed cells were treated with a 1000-fold diluted serum from an AIDS patient as a first antibody, and with a fluorescein isothiocyanate (FITC)-labeled anti-human IgG antibody (Capell) to detect HIV-infected (HIV-antigenic) cells. At least 500 cells/clone were microscopically observed to calculate the positive ratio. Accordingly, 17 clones (15 antigenic clones and two non-antigenic clone,) from H9 and 67 clones (63 antigenic clones and 4 non-antigenic clones) were selected for further characterization.

Next, each cell clone was tested to determine its ability to produce infectious HIV virion. Namely, a culture supernatant of each clone was passed through a nitrocellulose filter (0.22 μm, Millipore), and inoculated to MT-4 cells (Miyoshi, I. et al., Gann Monogr., 28. 219-228 (1982)) and MOLT-4 cells. These cells were then cultured in RPMI 1640 supplemented with 10% fetal calf serum under 5% $CO_2$ at 37° C., for at least 20 days, and were tested for HIV infection by the above-mentioned indirect immunofluorescence technique.

On the basis of a combination of an ability to express antigenic and an ability to infect MT-4 cells or MOLT-4 cells, the clones were classified into the following three groups:

Group I: clones which are antigenic and produce infectious HIV virion; these clones represent usual HIV-infected cells;

Group II: clones which are antigenic but do not produce infectious HIV virion; and Group III: clones which are nonantigenic and do not produce infectious HIV virion; these clones represent normal cells not infected with HIV.

The above classifications are summarized in Table 1.

TABLE 1

| Group | Expression of HIV antigen | Production of infectious virion | Classified clones/ total clones | |
|---|---|---|---|---|
| | | | Derived from H9 | Derived from MOLT-4 |
| I | + | + | 14/17 | 62/67 |
| II | + | − | 1/17 | 1/67 |
| III | − | − | 2/17 | 4/67 |

Among the above clones, those belonging to group II are within the scope of the present invention. As seen from Table 1, one clone obtained from an H9 cell line and one clone obtained from a MOLT-4 cell line were antigenic but did not produce infectious HIV virion. From the above two clones, a clone from the H9 cell line was selected for further characterization and designated as an H6 cell line.

The H6 cells ($3 \times 10^5$ cells/ml) were cultured for 3 days, and a supernatant and cells fraction were separated. The supernatant was diluted 100-fold and the cell fraction was diluted 1000-fold, and the diluted samples were assayed for the presence of p24 using an HIV antigen·EIA kit (Abbott). Note, the p24 is a protein having a molecular weight of 24 Kd encoded by a gene of HIV. The results are shown in Table 2.

TABLE 2

| | p24(CI)[a] | |
|---|---|---|
| Cell | Supernatant | Cell fraction |
| H6 | 6.66 | 16.74 |
| M12[b] | 9.70 | 1.43 |
| H9 | 0.40 | 0.42 |

[a]CI = cut off index; positive: >1.0 according to HIV antigen · EIA kit, Abbott
[b]M12 is HIV-infected MOLT-4 cell belonging to the group I; used as a positive control.

As seen from Table 2, the supernatant of H6 cells contained p24 in an amount comparable with that of the positive control M12, revealing that the H6 cells produce noninfectious HIV virion. Note, the H6 cells contained p24 in an amount as much as 12 times the amount of p24 in M12 cells. This means that a large amount of HIV antigen can be easily obtained by culturing H6 cells on a large scale, and extracting p24 from the cultured H6 cells.

The H6 cell line was further characterized.

Ability of H6 cells to form syncytia

Generally, an HIV-infected cell has syncytium-forming ability wherein the HIV-infected cell is fused with normal T cells to form a multi-nuclear cell (syncytium), resulting in the death of normal T cells. Therefore, in an HIV-infected patient, the immune defense ability is rapidly lowered, resulting in a high mortality rate.

Even if virion produced by an HIV-infected cell is noninfectious, if the HIV-infected cell has a syncytium-forming ability, the cell does not satisfy the requirements for a safe vaccine therapy and diagnosis of AIDS. Accordingly, the syncytium-forming ability of the H6 cells was evaluated according to a method of Tochikura, T. et al., Virology, 164, 542-546, 1988. Namely, H6 cells and MOLT-4 cells were co-cultured at a ratio of 1:1, and the number of cells were counted as time elapsed. If the H6 cell had a syncytium-forming ability, the number of cells decreased as a result of cell fusion. In this experiment, in addition to the H6 cells to be tested, HIV-infected H9 cells belonging to the above-mentioned group I, HIV-infected MOLT-4 cells belonging to the same group I, and HIV-infected MOLT-4 cells designated as M10 cells belonging to the group II were used as positive controls.

Figure 1:
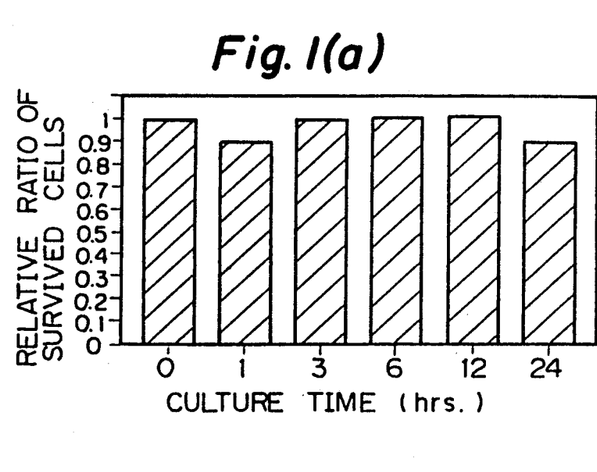
FIG. 1 illustrates graphs showing the results of tests to determine the syncytium forming ability of various cells.

The results are shown in FIG. 1 as a relative ratio of survived cells, calculated as follows:

Relative ratio of survived cells = number of co-cultured cells/(number of tested cells cultured alone + number of MOLT-4 cells cultured alone) ÷ 2. In FIG. 1, (a) represents a result of H6 cells, (b) represents a result of M10 cells, (c) represents a result of the above mentioned HIV-infected H9 cells, and (d) represents a result of the HIV-infected MOLT-4 cells. As seen from FIG. 1, the H6 cells of the present invention did not cause a reduction of the cell number, although other HIV-infected cells caused a dramatic reduction of the cell number. This means that only the H6 cells do not have a syncytium-forming ability. Note, even though the M10 cells produce a mutant HIV virion which is noninfectious but antigenic, and belongs to the group II, the M10 cell line has a syncytium-forming ability, and therefore, does not come within the scope of the present invention.

The above-mentioned experimental results show that the H6 cell is characterized by:

(1) producing mutant HIV virion which is noninfectious but antigenic; and (2) not having a syncytium-forming ability; and therefore, is a completely new type of HIV-infected cell Reverse transcriptase activity of virus produced by H6 cells H6 cells were cultured and 3 ml of the culture supernatant was centrifuged at 100,000 rpm for 30 minutes in a Beckman TL-100 centrifuge to recover virion as a pellet. The pellet was solubilized by a 0.1% NP40 detergent solution, and an ability of the solution to catalyze the incorporation of radio-labeled thymidine (manufactured by NEN) into an acid insoluble fraction was measured, using oligo dT-poly A (PL) as a template/primer in the presence of $Mg^{2+}$, and the reverse transcriptase activity calculated according to a method of Harada, S. et al., Science, 229, 563–566, 1985. As a result, the reverse transcriptase activity of the culture supernatant of H6 cells was found to be as low as that of the negative control H9 (not infected with HIV), revealing that H6 cells do not produce a reverse transcriptase. Note, positive control M12 cells clearly produced the enzyme. The results are shown in Table 3.

TABLE 3

| Cell | Reverse transcriptase[a] (c.p.m.) |
|---|---|
| H6 | 2,352 |
| M12 | 30,718 |
| H9 | 1,106 |

[a] Activity in 3 ml supernatant after culturing at $3.0 \times 10^5$ cells/ml for 3 days.

Properties of virion produced by H6 cell

To evaluate the properties of virion produced by H6 cells, the production of proteins of 17, 24, 34, 66, 41, 120 and 160 Kd encoded by gag, pol and env genes of HIV was determined. Namely, $1 \times 10^6$/ml of H6 cells were incubated with 100 $\mu$ Ci of 35S-methionine (NEN) in RPMI 1640 not containing methionine, for 6 hours, to label proteins, and cells and virion were solubilized with 0.1% NP40. For comparison, MOLT-4/HIV cells (HIV-infected MOLT-4 cells) were treated according to the same procedure as described above for H6 cells. Each of the thus-prepared samples was reacted with anti-HIV antibody positive and anti-HIV antibody negative human sera, and subjected to immunoprecipitation using protein A Sepharose (Pharmacia). After sodium dodecyl sulfate (SDS)-12% polyacrylamide gel electrophoresis according to a method of Laemmli, Nature, 227, 680–685 (1970), the gel containing $^{35}$S-methionine-labeled proteins was exposed to an X-ray film by fluorography using sodium salicylate. The results are shown in FIG. 2.

Figure 2:
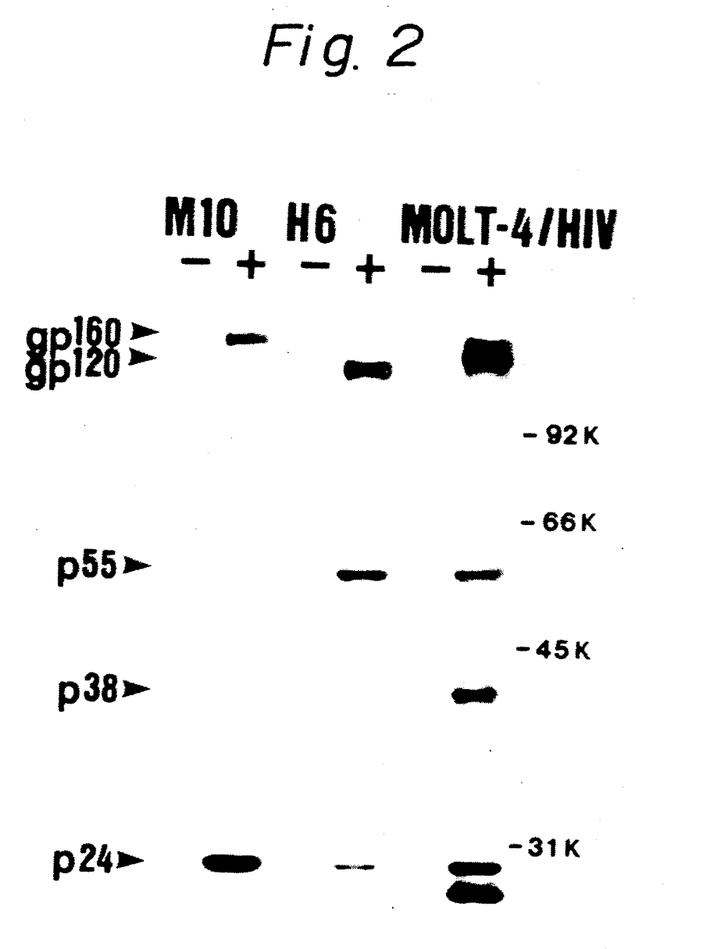
FIG. 2 shows the results of an electrophoresis of proteins derived from various viruses.

In FIG. 2, the symbol - represents a result of immunoprecipitation using an anti-HIV antibody negative serum, and the symbol + represents a result of immunoprecipitation using an anti-HIV antibody positive serum. The numbers on the right represent the molecular weight (Kd) of the molecular weight standards and their positions under the described condition. The symbols gp160, gp120, p55, p38, and p24 are names of authentic proteins derived from virus HTLV-III$_B$, and arrows on the right of the symbols represent the position of these proteins in the electrophoregram.

The results shown in FIG. 2 are summarized in Table 4.

The results in FIG. 2 shows a typical fluorography wherein exposure time was adjusted to visualize gp120 bands.

Table 4 shows the presence or absence of each protein.

TABLE 4

| Cell | gene protein | gag | | pol | | env | | |
|---|---|---|---|---|---|---|---|---|
| | | p17 | p24 | p34 | p66 | gp41 | gp120 | gp160 |
| H6 | | + | + | − | − | + | (+)[a] | (−)[b] |
| MOLT-4/HIV | | + | + | + | + | + | + | + |

[a] (+) shows that the protein is present but abnormal.
[b] (−) shows that the protein can be detected but in a very small amount.

As seen from Table 4, for H6 cells, although proteins p17, p24, gp41 and gp120 were detected by an anti-HIV antibody positive serum, reverse transcriptases p34 and p66 encoded by pol gene as well as gp160 were not detected. On the other hand, for the positive control MOLT-4/HIV, all proteins were detected. Taking into account the negative result obtained when using the anti-HIV antibody negative serum, it was confirmed that all of the detected proteins were derived from HIV.

The above-result shows that the noninfectious virion of the present invention produced by H6 cells essentially produces major virus proteins other than p66 and p34, and does not exhibit the reverse transcriptase activity provided by the p66 and p34.

The experiment described with reference to FIG. 2 was repeated using other anti-HIV antibody positive sera, and the same results were obtained. This shows that the noninfectious virion of the present invention reacts with sera from more than one AIDS patient, revealing that the antigenity of the present noninfectious virus is similar to that of an infectious virus. This point was further confirmed in Example 3.

Evaluation of RNA and provirus DNA of HIV in H6 cell

Whole RNA was extracted from H6 cells, and evaluated by Northern blot hybridization using an Sac I fragment of plasmid pNK5.2 (Yoshiyama, H. et al., Mol. Biol. Med., 4, 385–396, 1987) as a probe. Namely, 10 $\mu$g of whole RNA extracted from H6 cells was denatured by glyoxal, separated by 1% agarose gel electrophoresis, and the separated RNAs were transferred to a nitrocellulose membrane (BA85, manufactured by S&S). The RNAs were hybridized with the probe radioactively labeled by nick-translation using $^{32}$P-dCTP and a nick-translation kit N5000 (Amersham) ($2 \times 10^8$ d.p.m./$\mu$g DNA) in a hybridization medium containing 50% formamide, 5×SSC (1×SSC: 0.15M NaCl, 0.015M sodium citrate), 5×Denhardt's solution (1×Denhardt's solution: 0.02% bovine serum albumin, 0.02% Ficoll 400, 0.02% polyvinylpyrrolidone-40), 200 $\mu$g/ml salmon sperm single strand DNA, and 0.2% SDS, at 42° C. for 16 hours. Next, the membrane was washed with 2×SSC and 0.2% SDS, and then 0.1×SSC and 0.2% SDS, at 50° C., and exposed to an X-ray film (Fuji Film FR) at −80° C. for 12 hours.

For comparison, M10 cells and M12 cells were treated in the same manner as described for the H6 cells.

Figure 3:
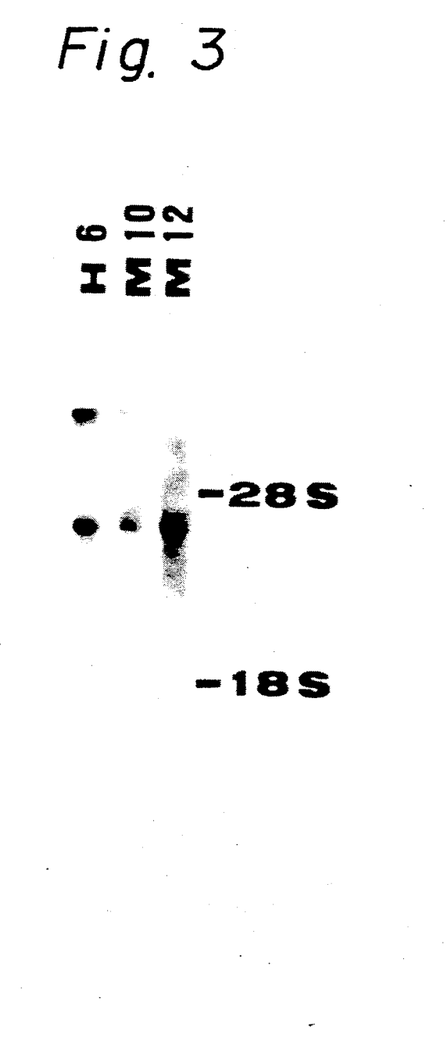
FIG. 3 shows the results of a Northern blot hybridization of total RNA derived from an H6 cell (lane a), M10 cell (lane b) and M12 cell (lane c), using a Sac I fragment of plasmid pNK5.2 as a hybridization probe.

The results are shown in FIG. 3. In FIG. 3, 28S and 18S represent the positions of ribosomal RNAs. As seen from FIG. 3, H6 cells provide 35S and 26S bands corresponding to entire mRNA and sub-genomic mRNA, respectively. Since the sizes of these mRNAs are the same as those from M12 cells, it is confirmed that H6 cells contain entire mRNA of HIV, and that the mRNA is normally spliced.

Next, the presence of provirus DNA in H6 cells was evaluated by Southern blot hybridization. Namely, DNA was extracted from H6 cells, and 5 $\mu$g of the DNA was cleaved with restriction enzyme Eco R I, Sac I or Bql II (Toyobo), and the digested DNA fragments were subjected to 0.7% agarose gel electrophoresis and transferred to a nitrocellulose membrane. The membrane was then subjected to hybridization with the above-mentioned probe radioactively labeled with 32P-dCTP ($2 \times 10^8$ d.p.m./$\mu$g DNA) in a hybridization medium containing 5 x SSC, 5 x Denhardt's solution, 200 $\mu$g/ml salmon sperm single strand DNA and 0.2% SDS, at 65° C. for 16 hours. After the hybridization, the filter was washed in 2×SSC and 0.2% SDS solution for 30 minutes at 25° C., and in 0.1×SSC and 0.2% SDS solution for 2 hours at 50° C., and exposed to an X-ray film (Fuji Film FR) at −80° C. for 2 hours.

For comparison, M10 cells and M12 cells were treated in the same manner as described for the H6 cells.

Figure 4:
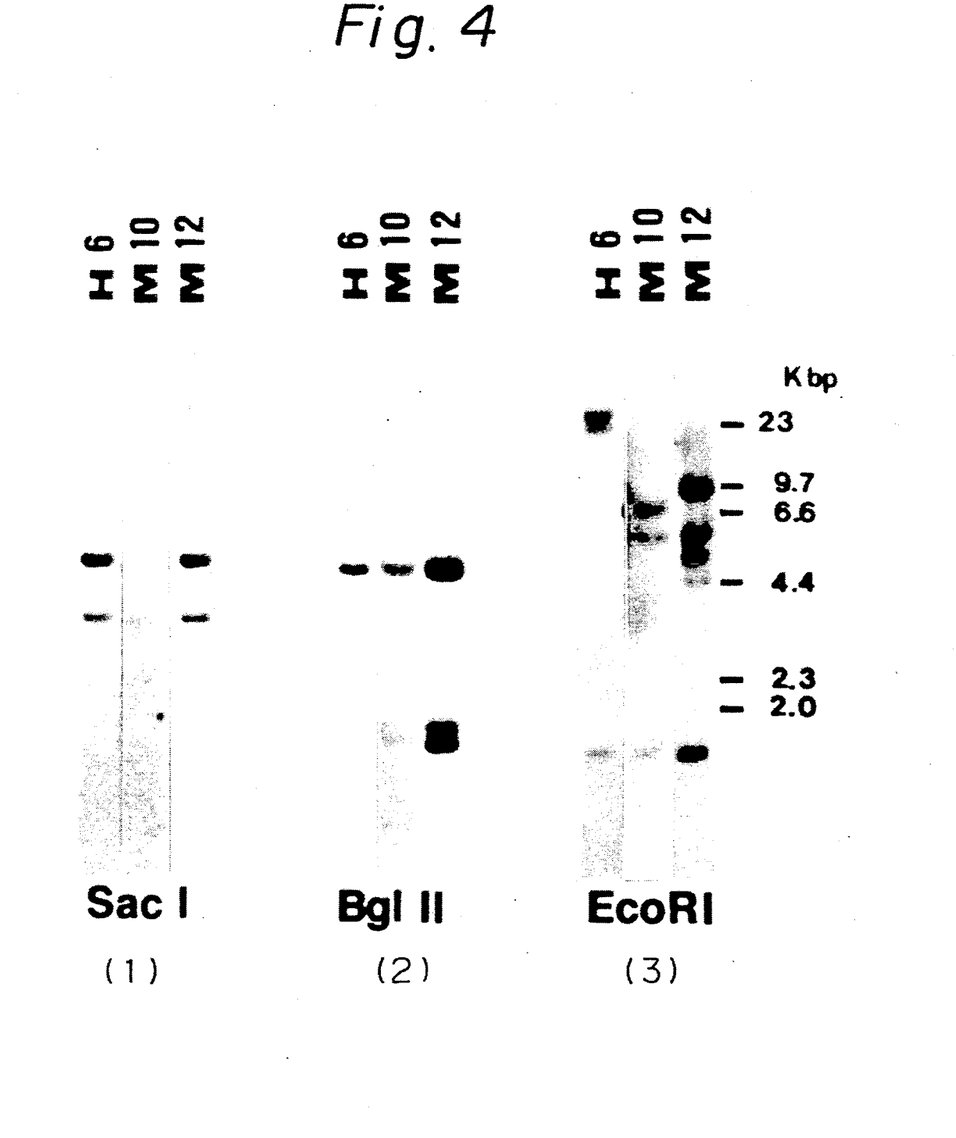

The results are shown in FIG. 4. In FIG. 4, the numbers on the right are molecular weights of the molecular weight markers, $\lambda$DNA Hind III fragments, and adjacent bars show the positions of the marker fragments.

It is expected from a restriction enzyme map of HIV (Ratner, L. et al., Nature, 313, 277–284, 1985), that the cleavage of DNA containing provirus DNA of HIV with Sac I will provide 4.5 Kbp and 3.5 Kbp provirus DNA fragments. As seen from FIG. 4, the Southern hybridization of Sac I-cleaved DNA of H6 cell origin provided bands corresponding to 4.5 Kbp and 3.5 Kbp, respectively. Moreover, the sizes of DNA fragments formed by Bcl II cleavage are identical among H6 cells, M10 cells, and M12 cells. This shows that the provirus DNA in H6 cells suffers no substantial deletion of DNA, and accordingly, that the conversion to a noninfectious virus relies on a mutation of a small region, such as a point mutation, on a virus genome. It is expected from a restriction cleavage map of HIV that the cleavage of genome DNA containing provirus DNA with Eco R I will provide two DNA fragments, i.e., provirus DNA fragment of about 1.2 Kbp, and provirus DNA fragment of about 4 Kbp accompanied by a host DNA fragment. As seen from FIG. 4, the cleavage of DNA derived from H6 cells with Eco R I provided bands corresponding to 1.2 Kbp, about 20 Kbp, and about 23 Kbp, upon Southern hybridization as expected above. Namely, the band of about 20 Kbp corresponds to a DNA fragment consisting of a provirus DNA fragment of about 4 Kbp and a host DNA fragment of about 16 Kbp, and the band of about 23 Kbp corresponds to a DNA fragment consisting of a provirus DNA fragment of about 4 Kbp and a host DNA fragment of about 19 Kbp. Since there are no detectable fragments other than those of 1.2 Kbp, 20 Kbp, and 23 Kbp, it is suggested that a single provirus DNA is incorporated in a DNA of the H6 cell. Conversely, a cleavage of DNA from M12 cells with Eco R I provides two other bands in addition to a band of 1.2 Kbp. This means that the H6 cells form a single clone containing a provirus DNA, but M12 cells form a population comprising more than one clone.

The above results clearly demonstrate that a single copy of an HIV provirus in an H6 cell is expressed as a virus RNA, and although the virus RNA is noninfectious, its size is the same as that of an infectious HIV.

Morphology of noninfectious virion produced by H6 cell

H6 cells were recovered by centrifugation in a precipitate fraction, and gently washed in serum-free RPMI 1640. The cells were then fixed in 2.5% glutaraldehyde in the presence of a 0.1 M sodium cacodylate buffer (pH 7.2), for 1 to 2 hours, and washed three times in a 0.1 M sodium cacodylate buffer containing 4% sucrose, each for 5 minutes. Next, the precipitate was treated with 1% osmium tetraoxide for 1 to 2 hours. The cells were washed three times in a 0.1M sodium cacodylate buffer, dehydrated stepwise with from 0% to 100% ethanol, and finally, with propyleneoxide. The cells were embedded in epoxy resin, which was then sliced to prepare thin sections, and the sections were then stained with lead acetate and uranyl acetate, and observed by a JEOL 200CX transmission electron microscope. As a control, M10 cells were treated and observed according to the same procedure as described above.

Figure 51:
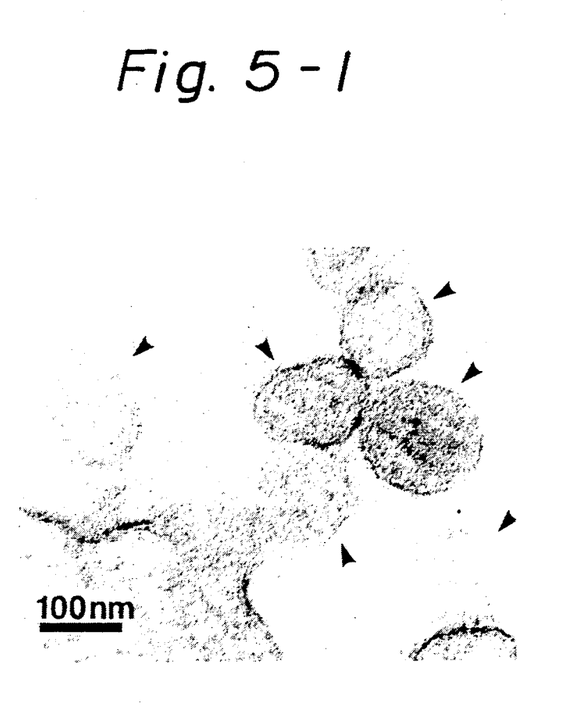
Figure 52:
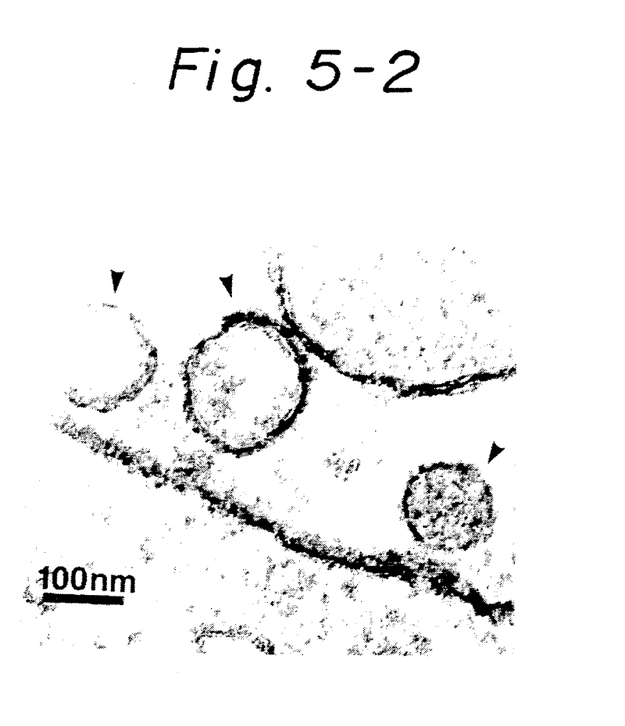

In FIGS. 5-1 and 5-2, virions produced by H6 cell (FIG. 5-1) and by M10 (FIG. 5-2) are shown by arrows. A retrovirus-like structure (virion) was observed on the surface of both the H6 cell and M10 cell, but surprisingly, the HIV virion from the H6 cell shows a condensed rod-shaped nucleoid which is a characteristic of the HIV virion, but the virion derived from M10 cell does not show such a characteristic, and is completely abnormal. Namely, a noninfectious virion prepared from H6 cells is morphologically identical with infectious HIV, and the morphological observation also expects the absence of a difference in antigenity between the present noninfectious HIV and the infectious HIV.

EXAMPLE 2

A virion obtained by the growth of H6 cells in RPMI 1640 for tissue culture was mixed with lactose 5 w/v%, saccharose 5 w/v%, D-sorbitol 1.8 to 2 w/v%, and hydrolyzed gelatin (2 to 3 w/v%), having a molecular weight of about 35,000, and the mixture was lyophilized to obtain live virus vaccines.

EXAMPLE 3

As a cellular antigen safe for use when carrying out an indirect immunofluorescence for a confirmatory diagnosis of a patient infected with HIV, H6 cells are used. Generally, antigenicity of HIV is believed to be easily changed, and therefore the cellular antigen desirably reacts with sera of as many patients as possible.

Figure 6A:
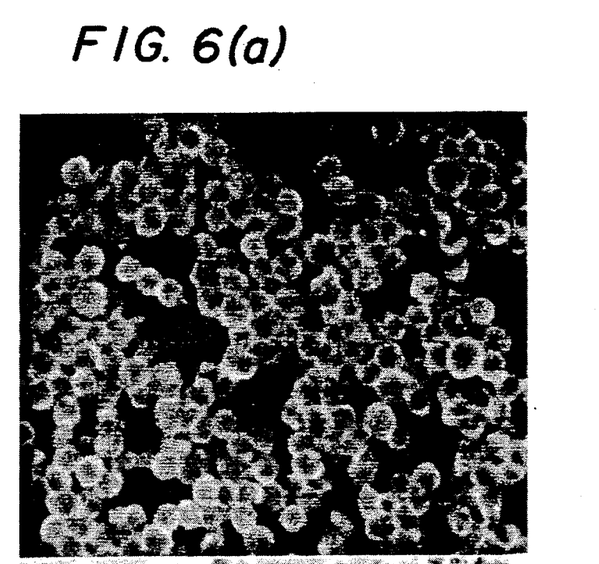
Figure 6B:
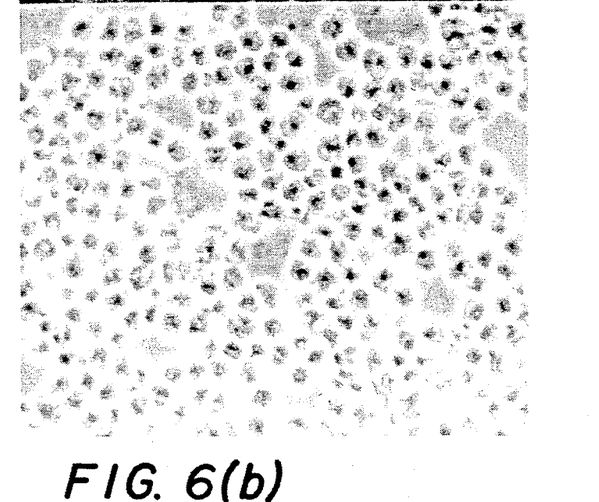

Accordingly, H6 cells were fixed on slide glasses by air-drying, followed by a treatment with cold methanol. These slides were then used for an assay of 26 serum samples from AIDS patients or hemophilia patients, as well as 24 serum samples from normal subjects, by indirect immunofluorescence using FITC conjugated goat anti-human IgG (Cappel) as a second antibody. As seen from Table 5, although the H6 cells did not react with all of the normal sera, they reacted with all of the infected sera, showing that the present H6 cells or the present noninfectious HIV reacts with a wide spectrum of HIV. Note, this result is partially exemplified in FIG. 6, wherein (a) represents a fluorescence micrograph and (b) represents a phase-contrast micrograph.

TABLE 5

| Results of confirmatory diagnosis by indirect immunofluorescence using H6 cells | | | |
|---|---|---|---|
| | | Result | |
| Sera from | No. of cases | Positive | Negative |
| Hemophilia and AIDS patients | 26 | 26 | 0 |

TABLE 5-continued

Results of confirmatory diagnosis by indirect
immunofluorescence using H6 cells

| Sera from | No. of cases | Result Positive | Result Negative |
|---|---|---|---|
| Normal subjects | 24 | 0 | 24 |

EXAMPLE 4

H6 cells were cultured in RPMI 1640 supplemented with 10% fetal calf serum at a concentration of 4 to 5 $\times 10^5$ cells/ml, and noninfectious virion was purified from the supernatant. The purified virion was used in a screening kit for a detection of an anti-HIV antibody in the ELISA, immuno blotting, and agglutination methods.

EXAMPLE

A provirus DNA fragment incorporated in H6 cells was used as a probe in a Northern blot hybridization analysis of HIV, and in a Southern blot hybridization analysis

EXAMPLE 6

H6 cells were cultured in the presence of a sample to be screened and $^{35}S$ methionine at a concentration of $3 \times 10^5$ cells/ml, for 20 hours. The cells and virus were solubilized by 0.1% NP40 and reacted with an anti-HIV antibody positive human serum. The mixture was precipitated with protein A Sepharose, the precipitate subjected to SDS-polyacrylamide gel electrophoresis, and the gel exposed to an X-ray film. The presence or absence of bands on the X-ray film, corresponding to proteins p17, p24, gp41 and gp120 of HIV origin, was observed to determine the anti-HIV activity of the sample. Where a band corresponding to one of the protein of HIV origin had disappeared, the sample was expected to exhibit an anti-HIV activity.

Further, H6 cells were cultured with a sample solution at a concentration of $3 \times 10^5$ cells/ml, for 3 days, and an amount of p24 in the culture supernatant measured using an HIV antigen·EIA kit (Abbott). Where an amount of p24 was reduced, the sample was expected to exhibit an anti-HIV activity.

The human T cell line H6 was deposited with Collection nationale di cultures de microorganismes Institut Pasteur (CNCM), 25 Rue du Docteur Roux 75724 Paris Cedex 15, France, as I-921, on Jan. 18, 1990.

We claim:

1. A cloned human T cell prepared by infecting a human T cell, H9, with HTLV-III B, which cloned human T cell is antigenic for HTLV-III B, does not have a syncytium-forming activity, and does not produce infectious HTLV-III B virion.

2. A cloned human T cell according to claim 1, producing antigenic, noninfectious HIV.

3. A cloned T cell according to claim 1, and designated as H6.

4. A process for producing a cloned human T cell according to claim 1, comprising the steps of:
    infecting human T cells, H9, with HTLV III B; and
    cloning and selecting a human T cell which is antigenic for HTLV III B, does not have a syncytium-forming ability and does not produce infectious HTLV III B virion.

* * * * *